(12) United States Patent
Lam et al.

(10) Patent No.: US 10,098,771 B2
(45) Date of Patent: Oct. 16, 2018

(54) CLIP SHEATH FOR A POLYMER SCAFFOLD

(71) Applicant: Abbott Cardiovascular Systems Inc., Santa Clara, CA (US)

(72) Inventors: Stan Lam, Pleasanton, CA (US); Erika Danielle Anderson-Bolden, Fremont, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 511 days.

(21) Appl. No.: 14/037,215

(22) Filed: Sep. 25, 2013

(65) Prior Publication Data

US 2015/0088240 A1  Mar. 26, 2015

(51) Int. Cl.
*A61F 2/958* (2013.01)
*A61F 2/97* (2013.01)

(52) U.S. Cl.
CPC ............. *A61F 2/958* (2013.01); *A61F 2/97* (2013.01); *A61F 2002/9583* (2013.01); *Y10T 29/49822* (2015.01); *Y10T 156/1002* (2015.01)

(58) Field of Classification Search
CPC .... A61F 2/97; A61F 2002/9583; A61F 2/958; Y10T 156/1002; Y10T 29/49822
See application file for complete search history.

(56) References Cited

U.S. PATENT DOCUMENTS

| | | | |
|---|---|---|---|
| 4,243,050 A | 1/1981 | Littleford |
| 4,581,025 A | 4/1986 | Sheath |
| 4,710,181 A | 12/1987 | Fuqua |
| 5,015,231 A | 5/1991 | Keith et al. |
| 5,158,545 A | 10/1992 | Trudell et al. |
| 5,211,654 A | 5/1993 | Kaltenbach |
| 5,250,033 A | 10/1993 | Evans et al. |
| 5,352,236 A | 10/1994 | Jung et al. |
| 5,458,615 A | 10/1995 | Klemm et al. |
| 5,545,211 A | 8/1996 | An et al. |
| 5,569,294 A | 10/1996 | Parkola |

(Continued)

FOREIGN PATENT DOCUMENTS

| | | |
|---|---|---|
| CN | 102300521 | 12/2011 |
| WO | WO 98/39056 | 9/1998 |

(Continued)

OTHER PUBLICATIONS

U.S. Appl. No. 13/644,347, filed Oct. 4, 2012, Wang.

(Continued)

*Primary Examiner* — Elizabeth Houston
*Assistant Examiner* — Tin Nguyen
(74) *Attorney, Agent, or Firm* — Squire Patton Boggs (US) LLP

(57) ABSTRACT

A sheath is placed over a crimped scaffold to reduce recoil of the crimped polymer scaffold and maintain scaffold-balloon engagement relied on to hold the scaffold to the balloon when the scaffold is being delivered to a target in a body. The sheath has an opening spanning the length of the sheath. The opening spans an arc length of about 90 degrees with respect to the circumference of the scaffold or balloon. The sheath may be removed from the scaffold by pinching the sheath between a thumb and forefinger, or bending or peeling back the sheath from the edges of the opening using fingertips.

20 Claims, 4 Drawing Sheets

(56) References Cited

U.S. PATENT DOCUMENTS

| | | |
|---|---|---|
| 5,591,226 A | 1/1997 | Trerotola et al. |
| 5,647,857 A | 7/1997 | Anderson et al. |
| 5,653,697 A | 8/1997 | Quiachon et al. |
| 5,693,066 A | 12/1997 | Rupp et al. |
| 5,709,703 A | 1/1998 | Lukic et al. |
| 5,749,852 A | 5/1998 | Schwab et al. |
| 5,765,682 A | 6/1998 | Bley et al. |
| 5,776,141 A | 7/1998 | Klein et al. |
| 5,782,855 A | 7/1998 | Lau et al. |
| 5,817,100 A | 10/1998 | Igaki |
| 5,868,707 A | 2/1999 | Williams et al. |
| 5,893,868 A | 4/1999 | Holman et al. |
| 5,964,730 A | 10/1999 | Williams et al. |
| 6,010,529 A | 1/2000 | Herweck et al. |
| 6,110,146 A | 8/2000 | Berthiaume et al. |
| 6,132,450 A | 10/2000 | Hanson et al. |
| 6,152,944 A | 11/2000 | Holman et al. |
| 6,197,016 B1 | 3/2001 | Fourkas et al. |
| 6,254,609 B1 | 7/2001 | Vrba et al. |
| 6,334,867 B1 | 1/2002 | Anson |
| 6,342,066 B1 | 1/2002 | Toro et al. |
| 6,355,013 B1 | 3/2002 | Van Muiden |
| 6,416,529 B1 | 7/2002 | Holman et al. |
| 6,447,540 B1 | 9/2002 | Fontaine et al. |
| 6,533,806 B1 | 3/2003 | Sullivan et al. |
| 6,749,584 B2 | 6/2004 | Briggs et al. |
| 6,783,542 B2 | 8/2004 | Eidenschink |
| 6,790,224 B2 | 9/2004 | Gerberding |
| 6,805,703 B2 | 10/2004 | McMorrow |
| 6,827,731 B2 | 12/2004 | Armstrong et al. |
| 6,899,727 B2 | 5/2005 | Armstrong et al. |
| 7,198,636 B2 | 4/2007 | Cully et al. |
| 7,314,481 B2 | 1/2008 | Karpiel |
| 7,347,868 B2 | 3/2008 | Burnett et al. |
| 7,384,426 B2 | 6/2008 | Wallace et al. |
| 7,618,398 B2 | 11/2009 | Holman et al. |
| 8,099,849 B2 | 1/2012 | Gale et al. |
| 8,414,528 B2 | 4/2013 | Liu et al. |
| 8,539,663 B2 | 9/2013 | Wang et al. |
| 8,539,993 B2 | 9/2013 | Hagano |
| 8,752,265 B2 | 6/2014 | Wang |
| 2001/0001128 A1 | 5/2001 | Holman et al. |
| 2002/0052640 A1 | 5/2002 | Bigus et al. |
| 2002/0099431 A1 | 7/2002 | Armstrong et al. |
| 2003/0004561 A1 | 1/2003 | Bigus et al. |
| 2003/0212373 A1 | 11/2003 | Hall et al. |
| 2004/0073286 A1 | 4/2004 | Armstrong et al. |
| 2004/0093005 A1 | 5/2004 | Durcan |
| 2004/0143315 A1 | 7/2004 | Bruunn et al. |
| 2006/0015171 A1* | 1/2006 | Armstrong ....... A61B 17/12022 623/1.12 |
| 2008/0010947 A1 | 1/2008 | Huang et al. |
| 2009/0221965 A1 | 9/2009 | Osypka |
| 2010/0004735 A1 | 1/2010 | Yang et al. |
| 2011/0184509 A1 | 7/2011 | Von Oepen et al. |
| 2012/0042501 A1 | 2/2012 | Wang et al. |
| 2012/0109281 A1 | 5/2012 | Papp |
| 2012/0261858 A1 | 10/2012 | Roberts et al. |
| 2012/0285609 A1 | 11/2012 | Wang |
| 2012/0324696 A1 | 12/2012 | Liu et al. |
| 2014/0096357 A1 | 4/2014 | Wang |
| 2014/0114399 A1 | 4/2014 | Hossainy et al. |
| 2014/0157567 A1 | 6/2014 | Wang |
| 2014/0379064 A1 | 12/2014 | Pacetti et al. |

FOREIGN PATENT DOCUMENTS

| | | |
|---|---|---|
| WO | WO 02/060345 | 8/2002 |
| WO | WO 2010/086320 | 8/2010 |
| WO | WO 2011/094048 | 8/2011 |

OTHER PUBLICATIONS

U.S. Appl. No. 13/708,638, filed Dec. 7, 2012, Wang et al.
U.S. Appl. No. 13/840,257, filed Mar. 15, 2013, Hossainy et al.
Angioplasty Summit Abstracts/Oral, The Am. J. of Cardiology, Apr. 23-26, 2013, p. 23B.
Bosiers et al., "Coronary and endovascular applications of the Absorb™ bioresorbable vascular scaffold", Interv. Cardiol. 4(6), pp. 621-631 (2012).
Miller "Abbott's Bioresorbable Stent Shows Durable Results in ABSORB Trial", The Gray Sheet, pp. 17-18, Mar. 2003.
International Search Report and Written Opinion for PCT/US/2014/057252, dated Jan. 22, 2015, 10 pgs.

* cited by examiner

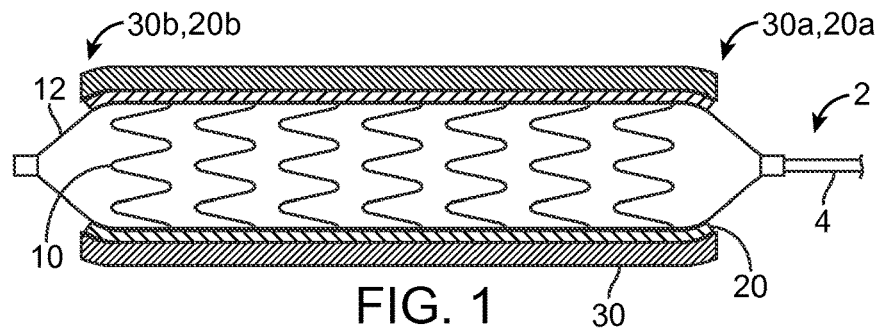
FIG. 1
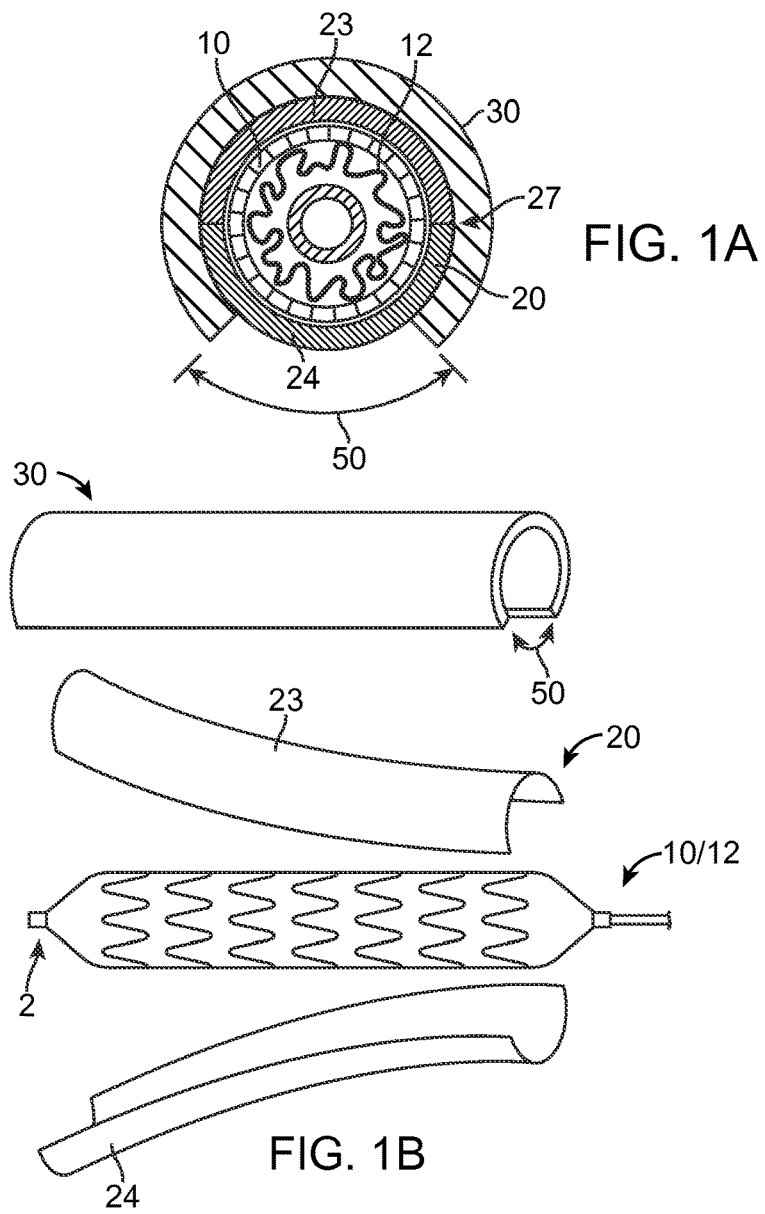
FIG. 1A
FIG. 1B

CLIP SHEATH FOR A POLYMER SCAFFOLD

FIELD OF THE INVENTION

The present invention relates to medical devices; more particularly, the invention relates to protective sheaths for scaffolds and stents crimped to a delivery balloon.

BACKGROUND OF THE INVENTION

A variety of non-surgical interventional procedures have been developed over the years for opening stenosed or occluded blood vessels in a patient caused by the buildup of plaque or other substances in the walls of the blood vessel. Such procedures usually involve the percutaneous introduction of an interventional device into the lumen of the artery. In one procedure the stenosis can be treated by placing an expandable interventional device such as an expandable stent into the stenosed region to expand and hold open the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands to a deployed or expanded state within a vessel when a radial restraint is removed, while the former relies on an externally-applied force to configure it from a crimped or stowed state to the deployed or expanded state.

Self-expanding stents formed from, for example, shape memory metals or super-elastic alloys such as nickel titanium (NiTi) which are designed to automatically expand from a compressed state when the radial restraint is withdrawn or removed at the distal end of a delivery catheter into the body lumen, i.e. when the radial restraint is withdrawn or removed. Typically, these stents are delivered within a radially restraining polymer sheath. The sheath maintains the low profile needed to navigate the stent towards the target site. Once at the target site, the sheath is then removed or withdrawn in a controlled manner to facilitate deployment or placement at the desired site. Examples of self-expanding stents constrained within a sheath when delivered to a target site within a body are found in U.S. Pat. No. 6,254,609, US 20030004561 and US 20020052640.

Balloon expanded stents, as the name implies, are expanded upon application of an external force through inflation of a balloon, upon which the stent is crimped. The expanding balloon applies a radial outward force on the luminal surfaces of the stent. During the expansion from a crimped or stowed, to deployed or expanded state the stent undergoes a plastic or irreversible deformation in the sense that the stent will essentially maintain its deformed, deployed state after balloon pressure is withdrawn.

Balloon expanded stents may also be stored within a sheath during a transluminal delivery to a target site and/or during the assembly or in the packaging of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating through interaction similar to forces at play when the blades and/or stent struts are misaligned during the diameter reduction. Examples of stents that utilize a sheath to protect the stent during a crimping process are found in U.S. Pat. No. 6,783,542 and U.S. Pat. No. 6,805,703.

A polymer scaffold, such as that described in US 20100004735 may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away after the scaffold has been implanted at the target vessel. The polymer scaffold described in US 2010/0004735, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it is believed that biodegradable scaffolds, as opposed to a metal stent, allow for improved healing of the anatomical lumen and reduced incidence of late stent thrombosis. For these reasons, there is a desire to treat a vessel using a polymer scaffold, in particular a bioresorbable polymer scaffold, as opposed to a metal stent, so that the prosthesis's presence in the vessel is for a limited duration. However, there are numerous challenges to overcome when developing a delivery system having a polymer scaffold.

Polymeric materials considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. Suitable polymers have a low strength to volume ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly a bioresorbable polymer such as PLLA or PLGA. Challenges faced when securing a polymer scaffold to a delivery balloon are discussed in U.S. patent application Ser. No. 12/861,719.

When using a polymer scaffold, several of the accepted processes for metal stent handling can no longer be used. A metal stent may be crimped to a balloon in such a manner as to minimize, if not eliminate recoil in the metal structure after removal from the crimp head. Metal materials used for stents are generally capable of being worked more during the crimping process than polymer materials. This desirable property of the metal can mean less concern over the metal stent—balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly often does not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site. Consequently, sheaths for metallic stents are often solely protective, preventing contamination or mechanical damage to the stent and coating. They do not need to be closely fitted to prevent stent recoil on aging and storage.

While a polymer scaffold may be formed so that it is capable of being crimped in such a manner as to reduce inherent elastic recoil tendencies in the material when crimped, e.g., by maintaining crimping blades on the scaffold surface for an appreciable dwell period, the effectiveness of these methods are limited. Significantly, the material generally is incapable of being worked to the degree that a metal stent may be worked without introducing deployed strength problems, such as excessive cracking in the material. Recoil of the crimped structure, therefore, is a problem that needs to be addressed.

In view of the foregoing, there is a need to address the challenges associated with securing a polymer scaffold to a delivery balloon and maintaining the integrity of a scaffold-balloon catheter delivery system up until the time when the scaffold and balloon are delivered to a target site within a body. Related to these objectives, there is a need to improve the design and handling of a sheath assembly that is removable (prior to implantation) without causing damage or dislodgment of the crimped scaffold underneath. There is also a need to improve upon sheaths for, or removal of sheaths from stents.

SUMMARY OF THE INVENTION

According to the invention, a two or three piece sheath can be removed from a scaffold (or stent) without sliding, and whose length can be kept close to the actual length of the crimped scaffold or stent, as needed. In one respect, the sheath includes a constraining sheath portion that applies an inwardly radial force upon a crimped scaffold to minimize recoil of the scaffold, yet may be removed from the scaffold without sliding and while not disrupting or moving an inner protecting sheath relative to the crimped scaffold. The constraining sheath may be removed by a pinching of the sheath or peeling or pulling away of sheath edges, which edges define a sheath opening that is formed to facilitate this removal of the constraining sheath from the inner protecting sheath.

In other respects, the invention is directed to sheaths and/or sheath assemblies used to maintain a polymer scaffold balloon engagement and delivery system profile as well as methods for assembly of a medical device including a balloon expandable polymer scaffold contained within a sheath. The invention is also directed to a sheath and methods for applying a sheath and sheath assembly that enables the sheath to be easily removed by a medical professional, e.g., a doctor, so as to minimize disruption to a crimped scaffold-balloon engagement or damage to the crimped scaffold. Sheaths and sheath assemblies according to the invention are removed before the medical device is introduced into a body. The invention is further directed to sheaths and their use with stents.

Sheaths according to the invention are particularly useful for maintaining scaffold-balloon engagement and desired delivery profile following a crimping process where the scaffold is crimped down to achieve a smaller crossing-profile, or crimped diameter. A scaffold formed at a larger diameter, near to or greater than the intended deployed diameter, can exhibit enhanced radial strength when supporting a vessel, as compared to a scaffold formed nearer to a crimped diameter. A scaffold formed near to a deployed diameter, however, increases the propensity for elastic recoil in the scaffold following the crimping process, due to the shape memory in the material. The shape memory relied on for enhancing radial strength at deployment, therefore, also introduces greater elastic recoil tendencies for the crimped scaffold. Recoil both increases the crossing profile and reduces the scaffold-balloon engagement needed to hold the scaffold on the balloon. In one aspect, the invention is directed to maintaining the crossing profile and/or maintaining balloon-scaffold engagement for scaffolds formed near to a deployed diameter.

In another aspect, the invention is directed to a method of assembly of a catheter that includes crimping a polymer scaffold to a balloon of the catheter and within a short period of removal of the scaffold from the crimper placing a restraining sheath over the scaffold. The steps may further include applying an extended dwell time following a final crimping of the scaffold (dwell times may be about 1, 2, 3, 4, 5, or about 3-5 minutes), followed by applying the restraining sheath. Both the crimping dwell time and applied restraining sheath are intended to reduce recoil in the crimped scaffold. The restraining sheath may include both a protecting sheath and a constraining sheath.

In another aspect, the invention is directed to a sterilized medical device, e.g., by E-beam radiation, contained within a sterile package, the package containing a scaffold crimped to a balloon catheter and a sheath disposed over the crimped scaffold to minimize recoil of the crimped scaffold. The sheath covers the crimped scaffold and may extend beyond the distal end of the catheter. The sheath is tubular and does not completely circumscribe the scaffold. The sheath has an opening spanning the length of the sheath. The opening has an arc length of less than 180 degrees and more preferably less than about 90 degrees with respect to the circumference of the scaffold or balloon partially circumscribed by the sheath. The sheath may be removed from the scaffold by pinching the sheath between a thumb and forefinger (see e.g., FIG. 3A), or by a bending or peeling back the edges of the sheath at edges of the opening using fingertips.

Sheaths arranged according to the invention provide an effective radial constraint for preventing recoil in a crimped scaffold, yet are comparatively easy to manually remove from the scaffold. A sheath that applies a radial constraint can be difficult to remove manually without damaging the crimped scaffold, dislodging or shifting it on the balloon. In these cases it is desirable to arrange the sheaths in a manner to apply an effective radial constraint yet make the sheaths capable of manual removal in a safe and intuitive manner. By making the sheath removal process easy to follow and intuitive, the possibility that a health professional will damage the medical device when removing the sheath is reduced.

A two-piece sheath for a polymer scaffold is described in U.S. Pat. No. 8,414,528 and U.S. application Ser. No. 13/924,421. Both components of the sheath may be made of PTFE. After the sheath is placed over the scaffold, the device (including the catheter) is inserted into a protective spiral coil made of LLDPE (linear low density polyethylene). At the point of use, prior to inserting the catheter into a body, a medical professional removes the catheter from the protective coil by pulling on a catheter hub and gently sliding the catheter out of the coil. In the next step, the catheter is grasped just proximal to the sheathed portion of the device, and with the other hand, an outer constraining sheath is slid distally. This frees an inner protecting sheath from the crimped scaffold because it is split in the region where the crimped scaffold resides. As the inner sheath is split or opens, it readily slides off. The catheter is then ready for being introduced into a body.

One possible issue presented by the sheath proposed in U.S. Pat. No. 8,414,528 is the required sliding action (i.e., sliding the outer sheath over the inner sheath) to remove the sheath form the scaffold. The sliding action necessitates a minimum clearance between the two sheath layers to ensure that frictional force created by the sliding does not exceed the material strength of the device (e.g., the catheter seals) and damage the device during sheath removal. A second possible issue with the proposed sheath design is its overall length. In order to free the crimped scaffold from the sheath pair in the designed way by sliding motion, the inner sheath (and, consequently, the entire length of the sheath) needs to be longer than the actual portion of the device requiring sheathing in order to ensure that the outer sheath has enough translational distance to slide distally along the inner sheath while maintaining a protecting sheath over the scaffold. For longer scaffolds (e.g., scaffolds indicated for the superior femoral artery) a correspondingly longer sheath is needed, which requires larger, more expensive packaging. Thus, the length of the sheath can impact the overall packaging size of the product.

In accordance with the foregoing, there is a scaffold (or stent), medical device, method for making such a scaffold, or method for assembly of a medical device (such as a scaffold-balloon catheter assembly) comprising such a scaffold having one or more, or any combination of the following things (1)-(28):

(1) A two or three-piece piece sheath disposed over the scaffold or stent.

(2) A constraining sheath may be removed by a pinching of the sheath or peeling or pulling away of sheath edges, which edges define a sheath opening that is formed to facilitate this removal of the constraining sheath from an inner protecting sheath. The outer sheath is removed before the inner sheath. To facilitate this removal a seam of the inner sheath is not placed within an opening of the outer sheath.

(3) A constraining and protecting sheath are removed simultaneously by pinching or peeling. To facilitate this alternative type of removal, although not necessary, it may be preferred to place a seam of the inner sheath within an opening of the outer sheath and/or the constraining sheath opening angle is relative small, such as about 5, 10, 15, or between 5 and 20 degrees.

(4) Ratio of crimped diameter to balloon nominal inflation diameter or expanded diameter is greater than about 2, 2.5 or greater than about 3 or 4; and/or the ratio of pre-crimp diameter to balloon nominal diameter is about 0.9 to 1.5.

(5) The catheter and scaffold are configured as a medical device suitable for being implanted within a body only after both a sheath disposed over the scaffold and a tube are removed. The medical device is not configured or even capable of being introduced into the body until after both the sheath pair and/or tube are removed from the medical device.

(6) A scaffold crimped to a balloon and a sheath disposed over the scaffold. The scaffold is configured for being introduced into a body only after the sheath is removed from the scaffold. And means for removing the sheath from the crimped scaffold in a safe manner. The means for removing in a safe manner may include an opening in the sheath having an arc-length of about 90 degrees or less than 180 degrees to facilitate or enable removal of the sheath by a pinching or pulling or peeling up upon edges defining the sheath opening using fingertips. The means may further include forming a non-circular outer surface, concave outer surface(s), a notch or ridges on the sheath outer surface.

(7) A method of maintaining a low crossing profile or retention between a scaffold and balloon, comprising: crimping; dwelling to reduce recoil; placing a first sheath over the scaffold; removing the first sheath; placing a second sheath; wherein prior to implantation the second sheath is removed. The second sheath is a two-piece sheath, such as the sheath described in FIG. 1A-1C or 4A-4C.

(8) The protecting sheath is a one or two piece sheath and/or the protecting sheath has a thickness that is about equal to, or 20%, 30%, 40% or 50% of the constraining sheath thickness.

(9) A constraining sheath length that is about, or is less, equal to, or greater than a protecting sheath length.

(10) The sheath may comprise PTFE, PVDF, fluoropolymer, polyethylene, polypropylene, nylon, nylon copolymers, Pebax, polyacetal, or polyimide.

(11) The polymer comprising the scaffold is bioresorbable, or the stent comprises a durable, non-bioresorbable, or non-bioerodible polymer.

(12) The scaffold may be crimped to a balloon catheter, the catheter may be contained within a tube and the catheter (with or without the tube) may be contained within an E-beam, ETO, x-ray or gamma-ray sterilized package.

(13) Crimping of the scaffold to the balloon includes placing a one-piece sheath over the scaffold immediately after crimping, removing the one-piece sheath and then placing a two-piece sheath over the scaffold, where the two-piece sheath is adapted for being removing by a medical professional prior to introduction to a body.

(14) A method of assembly including placing a catheter within a first tube wherein only the distal end of the catheter is outside the tube, crimping; and attaching a second tube to the first tube to cover the distal end. The tube may include a clearance at either distal or proximal end.

(15) A sheath pair satisfying two objectives: (1) apply a radial compressive force on a scaffold to minimize recoil, yet (2) be easily removed by a health professional in an intuitive manner, with reduced risk of causing damage to the scaffold or catheter when the sheath is removed.

(16) For the same material used for a protecting and constraining sheath, in which case a protecting sheath thickness is about equal to, or at least 20%, 30%, 40% or 50% and less than the thickness of the constraining sheath.

(17) A constraining sheath that circumscribes more than 50%, but less than the entire scaffold. An opening in the sheath therefore spans an arc-length less than about 180 degrees. In other aspects, a constraining sheath circumscribes more than 50%, 55%, 60%, 65%, 70% or 80% and less than the entire scaffold; the opening spans about 3%, 6%, 8%, 11%, 13%, 17%, 19%, 22%, 25%, 31%, 33% or 42% of the entire circumference of a scaffold; or the opening (expressed as an arc length) may be about 20-50, 80-120, 10, 20, 30, 50, 70, 90, or 110 Deg.

(18) When fully assembled the constraining and protecting sheaths are preferably arranged so that an entire one of the portions or halves of a two-piece protecting sheath are fully covered by the constraining sheath and the other only partially covered by the constraining sheath, or a seam (separating portions of the protecting sheath) or cut (separating halves of the protecting sheath) are not within the opening or uncovered part of the constraining sheath.

(19) A constraining sheath has an opening, a non-circular outer surface to facilitate a peeling-away or pinching of the constraining sheath to remove the constraining sheath from the protecting sheath, and/or a notch that is intended to cause a kinking or buckling of the sheath at the notch when radial-inward pressure is applied by fingertips that pinch, peel away or pull upon sheath edges defining a sheath opening. A constraining sheath according to embodiments may include the opening and a notch, the opening and a non-circular outer surface, or a combination of all three features.

(20) A constraining sheath that has a longitudinally extending notch. The notch may be located at a central point or along an axis of symmetry for the sheath. The sheath is configured to kink, fold or buckle at the notch when the constraining sheath is being removed from the protecting sheath.

(21) A constraining sheath that has one or more longitudinally-extending ridges. The ridges may be symmetrically disposed about an axis passing through the center of the catheter when the sheath is disposed over and constraining the scaffold. There can be one or two ridges on each side of the axis of symmetry.

(22) A constraining sheath that forms one or more concave surfaces on the outer surface of the sheath. The concave surfaces may be symmetrically disposed about an axis passing through the center of the catheter when the sheath is disposed over and constraining the scaffold.

(23) An apparatus, including a catheter including a scaffold comprising a polymer, the scaffold being crimped to a balloon and a constraining sheath disposed over the scaffold, the sheath comprising two edges defining an opening, the edges being circumferentially spaced from each other by between 5 Degrees and 150 Degrees; wherein the catheter is capable of being introduced into a body only after the sheath is removed from the scaffold.

(24) Any of the following things separately or in any combination with things (23), (25) or (26): wherein each of the two edges extend over the entire length of the sheath; wherein the between 50 Degrees and 150 Degrees circumferential spacing is about constant over the entire length; wherein the sheath has a non-circular outer surface; wherein the sheath has a notch and the sheath is symmetric about an axis passing through the notch and a longitudinal axis of the scaffold; wherein the sheath outer surface comprises a concave surface or the sheath outer surface comprises at least two longitudinally-extending ridges; further comprising, a protecting sheath disposed over the scaffold, wherein the protecting sheath is in direct contact with the scaffold and inside the constraining sheath; wherein the protecting sheath is a one or two piece sheath comprising halves or separate portions, respectively, wherein when the protecting sheath is disposed over the scaffold, edges of adjacent halves or portions are brought together to form a tubular body; wherein the edges of adjacent halves or portions are not within the opening defined by the constraining sheath edges; wherein the protecting sheath thickness is about 50% of the constraining sheath thickness; wherein the sheath is configured for being removed from the scaffold by pinching the two edges together, or by peeling the two edges away from each other as the sheath is lifted off the scaffold; wherein the sheath is not configured for being moved longitudinally relative to the scaffold when the sheath is being removed from the scaffold; a tube comprising the apparatus of claim 1 contained within a lumen of the tube.

(25) A method of making a medical device, comprising the steps of crimping the medical device to a balloon; and placing a constraining sheath over the crimped medical device, the constraining sheath comprising two edges defining an opening, when placed over the crimped medical device the edges are circumferentially spaced from each other by between 5 Degrees and 150 Degrees; wherein the medical device is capable of being implanted within a body only after the constraining sheath has been removed from the medical device. The method may further comprise: crimping the medical device to a balloon; placing a temporary sheath over the medical device; removing the temporary sheath from the medical device; and placing the constraining sheath over the medical device after the temporary sheath is removed;

(26) A tubular medical device, comprising: a sheath disposed over the medical device, wherein the medical device is configured for being radially expanded; the sheath circumscribing at most between about 70% to 98% of the medical device; wherein the medical device is capable of being introduced into a body only after the sheath is removed from the medical device. The medical device may be a stent or a scaffold.

(27) A method for removing a sheath from a crimped scaffold, comprising: applying pressure to opposite sides of the sheath; and pinching together, or peeling away edges of the sheath from the scaffold to remove the sheath from the scaffold.

(28) Edges of a constraining sheath or an outer sheath, when placed over a stent or scaffold, in a crimped condition, are circumferentially spaced from each other by between 5 to 20 Degrees or 50 to 150 Degrees.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 1 is a side cross-sectional view of a balloon catheter assembly, including a first embodiment of a constraining sheath and a protecting sheath disposed over a scaffold crimped to a balloon.

FIG. 1A is front view of the protecting and constraining sheaths, crimped scaffold and balloon of FIG. 1.

FIG. 1B is an exploded assembly view of the protecting and constraining sheaths and balloon catheter of FIG. 1.

FIG. 3A is a front view of the removal of the constraining sheath in FIG. 3, taken at section IIIA-IIIA.

DETAILED DESCRIPTION OF EMBODIMENTS

Figure 1C:
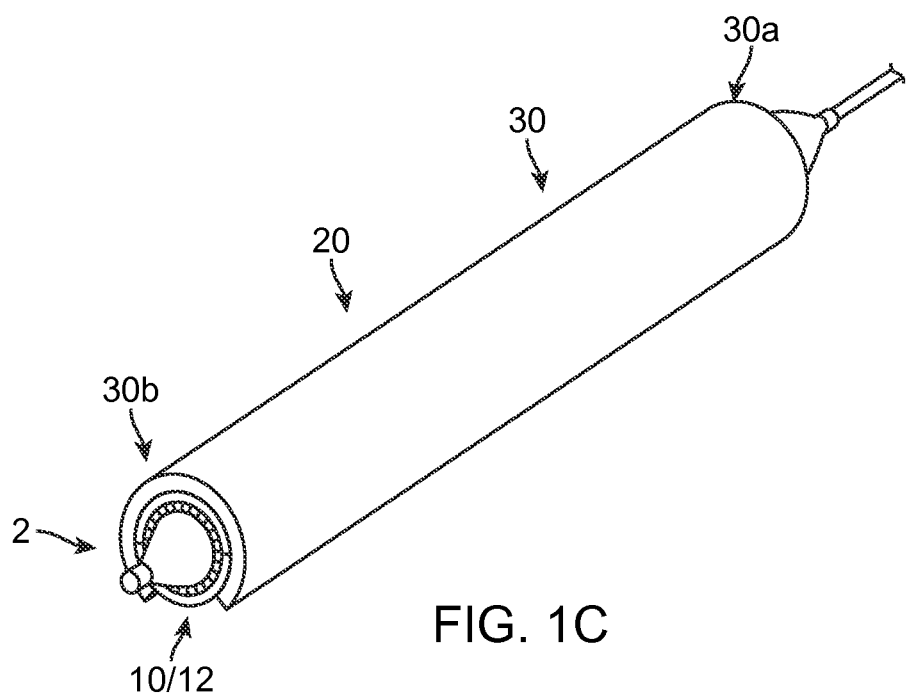
FIG. 1C is a perspective view of the balloon catheter of FIG. 1 with protecting and constraining sheaths.

For purposes of this disclosure, the following terms and definitions apply:

The term "about" means 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). It is understood that any numerical value, range, or either range endpoint (including, e.g., "about none", "about all", etc.) preceded by the word "about" in this disclosure also describes or discloses the same numerical value, range, or either range endpoint not preceded by the word "about".

The term "rigid" is a relative term used to describe something that is substantially stiffer than some other thing. For example, a first sheath or tube that is radially rigid, rigid in the radial direction, or simply rigid as compared to a second sheath or tube means that the first sheath/tube is incompressible compared to the second sheath, or essentially does not deform when an external, radially compressive force or pinching force is applied as compared to the second sheath, for the same applied load.

"Inflated diameter" or "expanded diameter" refers to the diameter the scaffold attains when its supporting balloon is inflated to expand the scaffold from its crimped configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for acute recoil in the scaffold.

A "pre-crimp diameter" means an OD of a tube, or the scaffold before it is crimped to a balloon. Similarly, a "final crimped diameter" means the OD of the scaffold when crimped to a balloon and removed from a crimping mechanism just prior to sheath placement. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter. A "partial crimp" diameter is a diameter attained after a scaffold or segment is crimped to a diameter less than a pre-crimp diameter and greater than the final crimp diameter. A partial crimp diameter can be an intermediate diameter after crimping from a pre-crimp diameter to about the nominal or over inflated diameter of the balloon to which the scaffold will be crimped. An example of a partial crimping diameter is described by the scaffold diameter following "Stage II" in FIGS. 3A and 4A, and described in U.S. application Ser. No. 13/644,347. A crimping mechanism or crimper may correspond to a linkage/mechanism including cooperating blades or teeth configured to apply an approximately uniform radial pressure on a scaffold to reduce its diameter to a final crimp diameter. The ratio of pre-crimp or intermediate crimp diameter to final crimped diameter may be greater than a ratio of expanded or post-dilation diameter (PDD) to the final crimped diameter of the scaffold. The crimping performed by the crimping mechanism may include a polymer material disposed between the teeth and surface of a scaffold; as example of such arrangement being found in US 2012/0042501.

"Recoil" means the response of a material following the plastic/inelastic deformation of the material and in the absence of externally applied forces, e.g., vessel contraction. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

"Axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. Thus, a link spaced 180 degrees from another link means 180 degrees as measured about the circumference of the tubular construct.

"Radial" refers to a direction, orientation, or line that is perpendicular or substantially perpendicular to the central axis of the stent or the central axis of a tubular construct and is sometimes used to describe a circumferential property, i.e. radial strength.

A "stent" is a permanent structure, usually comprised of a metal or metal alloy, generally speaking, while a "scaffold" will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure. Some material used to make a stent and/or scaffold structure is listed in U.S. Pat. No. 8,099,849.

"Radial strength" and "radial stiffness" adopts the definitions found in Ser. No. 13/842,547 filed Mar. 15, 2013.

A polymer scaffold according to a preferred embodiment is formed from a radially expanded or biaxially expanded extruded tube comprising PLLA. The degree of radial expansion (RE) and axial expansion (AE) that the polymer tube undergoes can characterize the degree of induced circumferential molecular and crystal orientation as well as strength in a circumferential direction. In some embodiments the RE is about 400% and the AE is 40-50%. Other embodiments of processing parameters, RE and AE expansions considered within the scope of the disclosure are found in U.S. application Ser. No. 13/840,257 filed Mar. 15, 2013.

The scaffold is laser cut from the expanded tube. The diameter of the tube is preferably selected to be about the same, or larger than the expanded diameter or PDD for the scaffold to provided desirable radial strength characteristics, as explained earlier. The scaffold is then crimped onto the balloon of the balloon catheter. Preferably, an iris-type crimping mechanism is used to crimp the scaffold to the balloon.

The pre-crimp memory in the scaffold material following crimping will induce some recoil when the scaffold is removed from the crimper. While a dwell period within the crimper can reduce this recoil tendency, there is residual recoil to restrain while the scaffold awaits use. This is done by placing a restraining sheath over the scaffold after the crimper blades are released and the scaffold removed from the crimper head. This need to reduce recoil is particularly evident when the diameter reduction during crimping is high, e.g., as in above examples, since for a larger starting diameter compared to the crimped diameter the crimped material can have higher recoil tendencies. Examples of polymers that may be used to construct sheaths described herein are Pebax, PTFE, polyethylene, polycarbonate, polyimide and nylon. Examples of restraining sheaths for polymer scaffold and methods for attaching and removing restraining sheaths for polymer scaffold are described in US20120109281, US20120324696 and U.S. Pat. No. 8,414,528, and U.S. application Ser. No. 13/708,638.

FIGS. 1 and 1A show a side cross-sectional and front view, respectively, of a distal end of a scaffold-balloon catheter assembly 2. The catheter assembly 2 includes a catheter shaft 4 and a scaffold 10 crimped to a delivery balloon 12. As shown there are two separate sheaths 20, 30 disposed over the scaffold 10. The scaffold 10 is contained within a protecting sheath 20 and a constraining sheath 30, which is placed over the outer surface of the protecting sheath 20 to position it over the scaffold 10. Before inserting the catheter assembly 2 distal end within a patient, both the constraining sheath 30 and protecting sheath 20 are removed by a health professional. The protecting sheath has a distal end 20b and a proximal end 20a. The constraining sheath has a distal end 30b and a proximal end 30a.

The sheaths 20, 30 provide an effective radial constraint for reducing recoil in the crimped scaffold 10. Yet the sheaths 20, 30 are also easily removed by a health professional at the time of a medical procedure by removing the outer sheath 30 from the inner sheath 20. As described herein, a sheath that applies a radial constraint can be difficult to manually remove without adversely affecting the structural integrity of the medical device. In these cases, it is desirable to arrange the sheaths so that special handling is not required by the health professional when the sheath is manually removed. By making the sheath removal process easy to follow or intuitive, the possibility that a health professional will damage the medical device by improperly removing the sheath is reduced.

The constraint imposed by the sheaths 20, 30 may be such as to maintain the scaffold 10 at essentially the same, or close to the same diameter it had when removed from the crimping mechanism. In some embodiments a first sheath, e.g., a polymer tube with weakened line and/or V-notch and configured for being torn when removed from the scaffold, is applied immediately after crimping and may apply a higher crimping force than the sheaths 30 and 20. Preferred embodiments of such a sheath and process for applying the sheath to a crimped scaffold are described in U.S. application Ser. No. 13/708,638. This first sheath is removed shortly after crimping, e.g., within ½ to one hour after crimping. Then sheaths 30 and 20 are applied. The sheath 30 is tightly fit over the sheath 20 and scaffold 10 so that the radial inward force applied on the scaffold 10 can prevent or reduce recoil in the scaffold 10 while the finished product is packaged and awaiting use. The health professional then removes both sheaths at the time of the medical procedure. As such, any potential recoil in the scaffold 10 prior to using the medical device is minimized. The sheath 30, although imposing a tight fit on the scaffold 10 (through sheath 20), can be manually removed by a health professional such as by the technique illustrated in FIGS. 3 and 3A. This manner of removal, enabled by the construction of sheath 30 and 20, avoids excessive longitudinal pulling forces that can result in damage to the scaffold, catheter, or dislodge the scaffold from the balloon. It also minimizes the overall length of the sheathed scaffold, which can be important for peripherally-implanted scaffolds, which can have lengths up to about 200 mm.

The inner sheath 20 and outer sheath 30 may alternatively be thought of as a protecting sheath 20 and constraining sheath 30, respectively. When the scaffold 10 is constrained by sheath 30, as in FIG. 1, the constraining sheath 30 is located over the section of the protecting sheath 20 where the crimped scaffold 10 is found. This sheath 30 is made from a polymer tube material having a thickness and pre-stressed inner diameter size suitably chosen to cause the sheath 30 to apply a radially inward directed force on the scaffold 10. The thicker the tube and/or the smaller the pre-stressed inner diameter size for the sheath 30 the higher this constraint will be on the scaffold 10. However, the sheath 30 thickness should not be too thick, nor its inner diameter too small as this will make it difficult to remove the sheath 30 from the scaffold 10. If excessive force is needed to reposition the sheath 30, the scaffold 10 can dislodge from the balloon 12 or the scaffold 10 and catheter shaft 4 can become damaged when the sheath 30 is moved.

If only sheath 30 were applied, i.e., the sheath 20 is not present, the amount of preload that the sheath 30 could apply to the scaffold 10 without affecting scaffold-balloon engagement would be limited (pre-load refers to the sheath's ability to apply a radially compressive force on the scaffold or stent to minimize recoil and/or maintain the sheath over the scaffold during transport or handling). However, by introducing the protecting sheath 20 between the scaffold-balloon surface and sheath 30 the sheath 30 can impose a higher preload on the scaffold 10 without risk to the integrity of the scaffold-balloon engagement when the sheath 30 is applied to and/or removed from the scaffold 10. The sheath 20 also protects a coating on the surface of the scaffold or stent while the sheath 30 is being removed. The protecting sheath 20 therefore serves to protect the integrity of the scaffold and/or scaffold-balloon structure as the sheath 30 is repositioned relative to the scaffold 10. Examples of one-piece and two-piece sheaths capable of performing in a similar manner are found in US2012/0324696.

Figure 2:
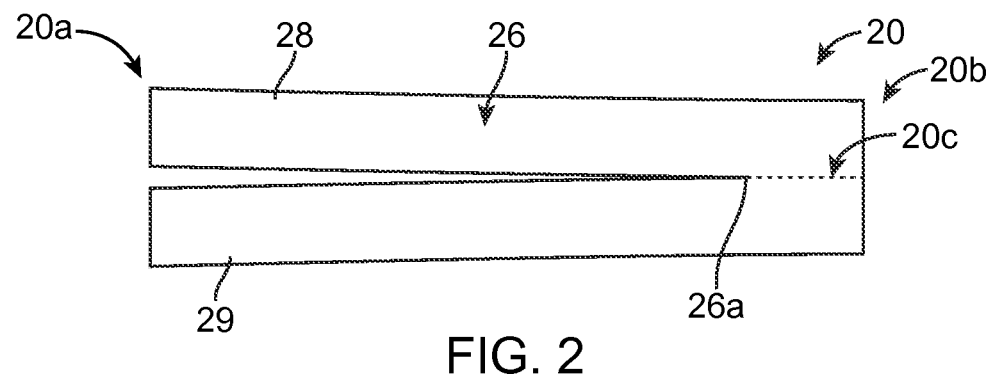
FIG. 2 is a second embodiment of a protecting sheath.

Again referring to FIGS. 1, 1A, 1B and 1C, the protecting sheath 20 extends over about the entire length of the scaffold (as shown) and may extend beyond the distal tip of the catheter assembly 2. The protecting sheath 20 is preferably formed from a unitary piece of polymer material, which is shaped to protect the scaffold/balloon 10/12. The protecting sheath may be configured as a two piece protecting sheath 20 having two separate portions 23 and 24, as illustrated in FIG. 1B, or as a one-piece protecting sheath having a cut 26 defining separate halves 28, 29, as illustrated in FIG. 2. In the case of a one-piece sheath, the cut 26 may begin at a proximal end 20b at 26a. There may be a weakened line 20c to facilitate a tear away of the two halves 28, 29 to separate one from the other, or there may be no weakened line from the start of the cut 26 to the distal end 20b. The halves 29, 28 are configured to freely move apart when the sheath 30 is positioned towards the distal end 20b. In some embodiments, the location 26a is a living hinge 26a about which the upper half 29 and lower half 28 of the sheath 20 can rotate, or deflect away from the scaffold 10 when the sheath 30 is removed. The protecting sheath 20 prevents direct contact between the constraining sheath 30 and the surface of the scaffold 10. After the sheath 30 is removed, the protecting sheath 20 is easily removed due to the presence of halves 23, 24 or 28 and 29, that preferably provide about no radial compressive force on the scaffold-balloon 10/12, as compared to a cylindrical tube that must be slid across the balloon-scaffold when removed. Alternative embodiments of a two-piece protecting sheath are described in FIGS. 11-12 of US2012/0324696.

Referring once again to FIGS. 1, 1A, 1B and 1C there are views of the constraining sheath 30 portion of the sheath. The constraining sheath 30 circumscribes less than all of the sheath and balloon 10/12 when disposed over the scaffold 10/12 and protecting sheath 20, as represented by the opening 50. The sheath 30 is preferably configured in this way to jointly serve two conflicting objectives: (1) apply a radial compressive force on the scaffold 10 to minimize recoil, yet (2) be easily removed by a health professional in an intuitive manner, with reduced risk of causing damage to the scaffold or catheter (see FIG. 3) when the sheath 30 is removed.

Since the sheath 30 is not entirely cylindrically and only partially circumscribes the scaffold 10 (as can be appreciated from the views in FIGS. 1A, 1B and 1C) there is not a radial force applied directly by the sheath 30 about the entire circumference. However, it was found that objective (1) is met if the sheath 30 is combined with an inner protecting sheath 20 of appropriate thickness or radial stiffness. With such a matching, objective (1) could still be satisfied; that is, radial forces imposed by the scaffold 30 produces a sufficiently uniform radial constraint such that there is maintained a substantially a circular cross-section and limited recoil of the scaffold during a prolonged shelf-life for the medical device. For example, assuming both sheaths 20, 30 are made from the same material, objective (1) may be met when sheath 20 is at least 20%, 30%, 40% or 50% less than the thickness of sheath 30. This relative thickness will enable sheath 20 to effectively distribute the radial compressive load across the uncovered portion of the scaffold 10, i.e., the opening 50 shown in FIGS. 1A and 1B. If the sheath 20 is too thin, then its radial stiffness is low and the radial compression loading does not distribute across the section of scaffold 10 exposed by the opening 50. Additionally, it will be appreciated that the larger the opening 50 the more thick the sheath 20 should be, as the sheath 20 is called upon more to distribute the radial compressive loads across the opening 50 (so as to create the desired radial loading that limits recoil and maintains a circular cross section when opening 50 is increased in size).

In some embodiments the sheath 20 can have a minimum thickness of 100 microns or less than 100 microns, or 500 microns. The sheath 20 can have a thickness that is 5% of the sheath 30 thickness.

Figure 3:
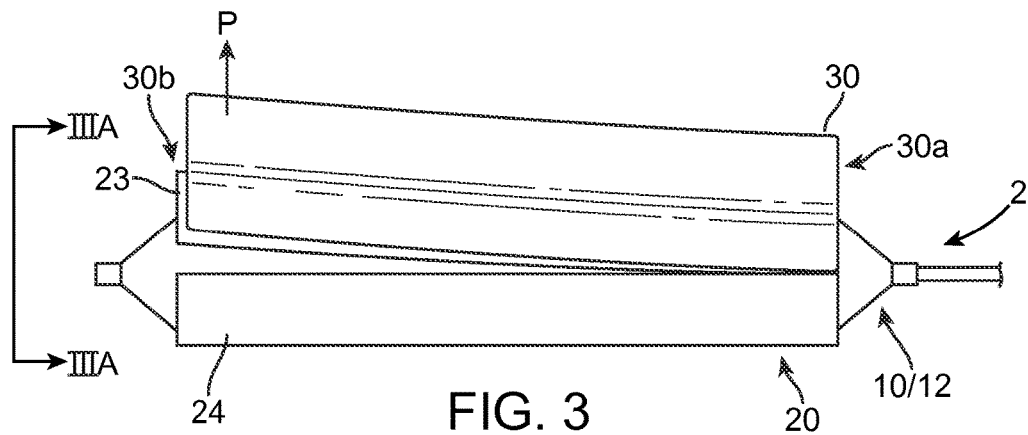
FIGS. 3 and 3A are drawings showing a method of removal of a constraining sheath from a protecting sheath, the protecting sheath covering a scaffold crimped to a balloon.
Figure 3A:
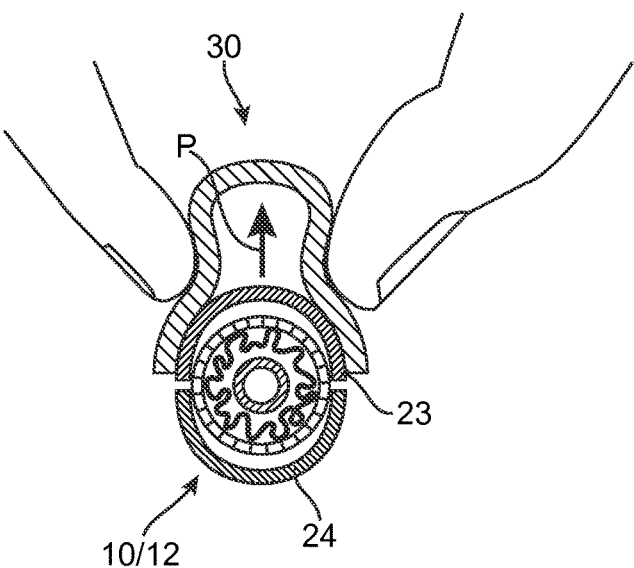

The amount less than the entire scaffold 10 circumscribed by sheath 30, or the uncovered amount (e.g., as an arc length or % opening) will be referred to as opening 50. As can be appreciated from FIG. 1B the opening 50 may be constant across the entire length of the constraining sheath 30. With respect to objective (2) (above) the greater the opening 50 (FIG. 1A) the more easily the sheath 30 may be removed by, e.g., pinching it off the sheath 20, as indicated in FIGS. 3 and 3A. However, the opening 50 cannot be too great as this might cause either the sheath 30 accidentally removed, or removed simultaneously with the sheath 30, which might lead to damage to the scaffold, or result in the combined sheaths 20, 30 not being capable of applying a sufficiently effective radial compressive force about the scaffold to minimize recoil and/or maintain about a circular crimped scaffold, i.e., no outward bulging of the uncovered scaffold portion as a result of unrestrained recoil.

Consistent with objectives, the sheath 30 should circumscribe more than 50%, but less than the entire scaffold 10, to facilitate removal from sheath 20 without disturbing the relationship between the sheath 20/scaffold 10. Opening 50 therefore spans an arc-length less than about 180 degrees. In other aspects, the sheath 30 may circumscribe more than 50%, 55%, 60%, 65%, 70% or 80%, but not the entire scaffold 10; the opening 50 may span about 3%, 6%, 8%, 11%, 13%, 17%, 19%, 22%, 25%, 31%, 33% or 42% of the entire circumference of the scaffold 10; or the opening 50 (expressed as an arc length) may be about 20-50, 80-120, 10, 20, 30, 50, 70, 90, or 110 Deg.

According to another aspect, in keeping with objectives (1) and (2), when fully assembled the sheaths, 20, 30 are preferably arranged so that an entire one of the portions 23, 24 or halves 28, 29 are fully covered by the sheath 30 and the other only partially covered by the sheath 30, or the seam 27 (separating portion 23 and 24) or cut 26 (separating halves 28, 29) are never within the opening 50 or uncovered by the sheath 30. This arrangement is shown in FIG. 1A. In this preferred embodiment the portion 23 is fully covered and the portion 24 partially covered by the sheath 30, or nowhere is seam 27 within the opening 50. By this arrangement, the pinching process (FIG. 3, 3A) can best preclude both sheaths 20, 30 being (unintentionally) removed simultaneously, which is not preferred although acceptable in some embodiments. If, in contrast, the seam 27 were located within the opening 50 (e.g., seams 27 were located 90 degrees from the position shown in FIG. 1A), then a pinching and lifting up of the sheath 30 of the sheath 30 (FIG. 3A) might also remove the sheath 20. If both sheaths 20, 30 are removed simultaneously then there may be damage to the scaffold 10 because the pinching of the fingers (FIGS. 3, 3A) in combination with the sheath 30 removal would cause the sheath 20 to pull across the surface of the scaffold 10 and/or balloon 12 surface.

In an alternative embodiment sheath 20 and 30 may be removed simultaneously. In one example this may be achieved by placing the seam 27 within the opening 50. Additionally, the opening may span a relatively small angle to cause both sheaths 20, 30 to be removed at the same time. For example the angle may be about 5, or 15 degrees. Thus, for a seam within the opening 50 and/or the angle about 5, 10, 15, or between 5 and 20 degrees a pinching or peeling away of the sheath 30 will also pinch or peel away sheath 20.

According to another aspect of the disclosure, a constraining sheath may have an opening 50, a non-circular outer surface to facilitate a peeling-away or pinching of the constraining sheath to remove the constraining sheath from the protecting sheath, and/or a notch intended to cause buckling or kinking of the sheath, thereby causing it to suddenly lose transverse stiffness when the sheath 30 edges defining the opening 50 are pinched together or pulled apart. All these features are intended to facilitate an easier removal of a constraining sheath from a protecting sheath in the manner shown in FIGS. 3-3A.

Figure 4A:
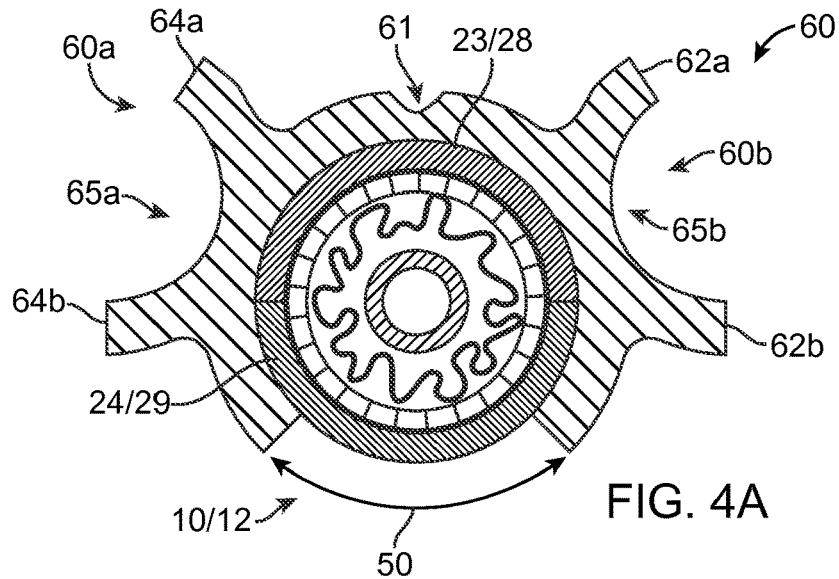
FIGS. 4A, 4B and 4C are front, perspective and partial perspective views of the balloon catheter with the protecting sheath of FIG. 1, and a second embodiment of a constraining sheath.
Figure 4B:
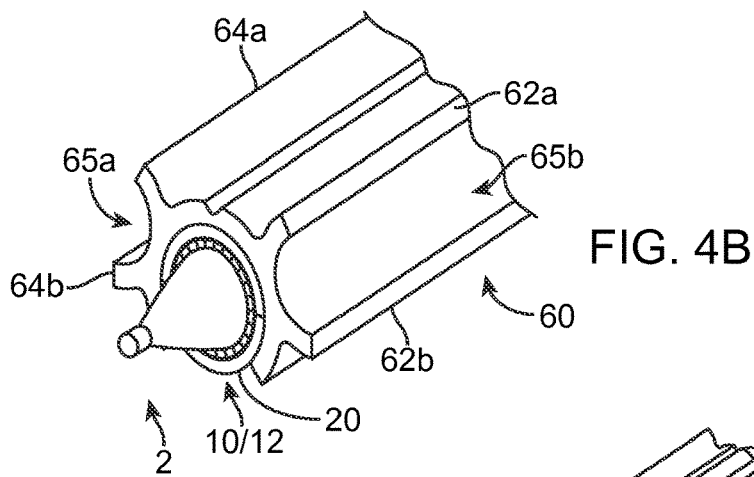
Figure 4C:
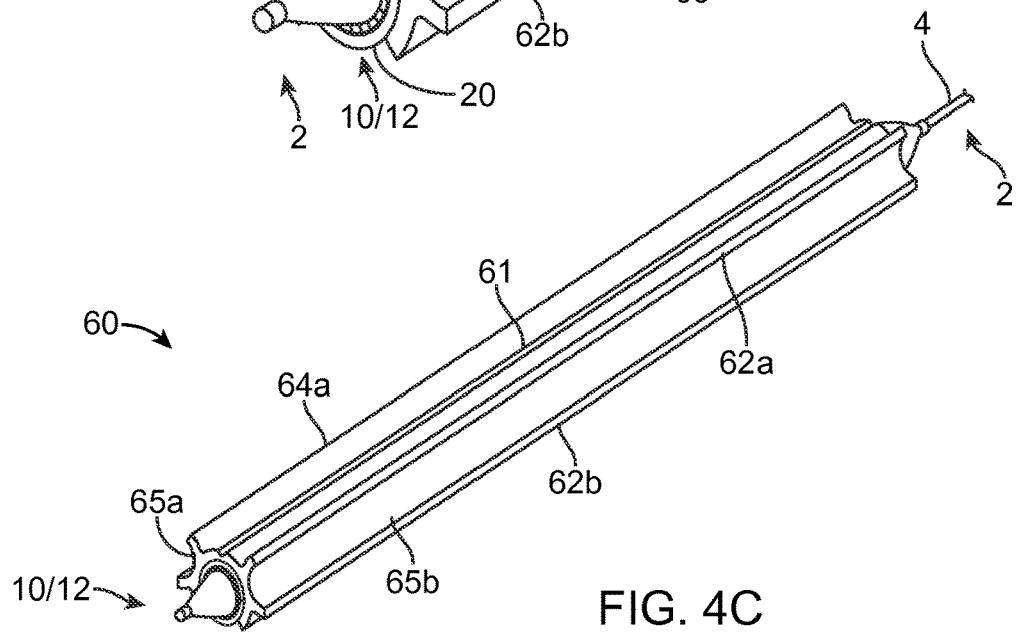

FIGS. 4A-4C illustrate a constraining sheath 60 having the opening 50 (as in the case of sheath 30), the notch and non-circular outer surface features. A constraining sheath according to embodiments may include the opening 50 and a notch, the opening and a non-circular outer surface, or a combination of all three features as in the illustrated embodiment.

In one embodiment, the non-circular surface for the sheath 60 includes ridges 62a, 62b, 64a, 64b. The sheath 60 also includes a notch 61 formed on the outer surface, inner surface or both outer and inner surfaces at about the location shown, which separates a first portion 60a and second portion 60b of sheath 60. Portions 60a and 60b are symmetric about an axis passing through the notch 61 and center of the scaffold-balloon 10/12 in FIG. 4A. As can be appreciated from the substantially reduced thickness at the notch 61 compared to other portions of the sheath 60, the notch 61 facilitates a folding, kinking or buckling of the sheath 60 at the notch 61 when the sheath 60 is removed from the sheath 20 in the manner shown in FIG. 3A. This can impose less difficulty on the health professional removing the sheath 30, because when the sheath 60 buckles at the notch 61 there is less resistance to deformation by the sheath 60 when the edges are pinched together (FIG. 3A) or pulled apart.

Referring again to FIGS. 4A-4C, portion 60a of the sheath 60, as in the case of portion 60b, has two longitudinally-running ridges 64a, 64b. Preferably these ridges 64a, 64b form a concave surface 65a, in contrast to the convex outer surface of sheath 30 (or the portion of sheath 60 outer surface exclusive of concave surfaces 65a, 65b). Similarly, portion 60b has ridges 62a, 62b and concave surface 65b. The concave surfaces 65a, 65b, which may each have a circumferential extent about the average width of a fingertip, provides a surface that engages the fingertip to facilitate sheath 60 removal from the scaffold. Alternatively, a pair of the ridges 62, 64 may be engaged (one with each finger) to lift the sheath 60 off of the sheath 20.

In alternative embodiments include, in any combination: ridges pairs 62 and 64 may extend only partially or over a portion of the sheath 60, such as two pair (symmetrically disposed about the axis passing through the notch 61 and center of the scaffold 10) or all four of the ridges 62, 64 being located only at about the distal end of the sheath 60; the notch 61 being located only at about the distal end; and the surfaces 65a, 65b being convex as opposed to concave as shown.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. An apparatus, comprising:
   a catheter including a scaffold comprising a polymer, the scaffold being crimped to a balloon;
   a constraining sheath disposed over the scaffold, the constraining sheath comprising two edges defining an opening, the edges being circumferentially spaced from each other by between 5 Degrees and 150 Degrees; and
   the constraining sheath further comprising a concave outer surface located on each of opposite sides of the opening, wherein each concave outer surface is between two convex outer surfaces, one of the two convex outer surfaces comprising one of the two edges; and
   a protecting sheath comprising first and second halves disposed over the scaffold and inside the constraining sheath;
   wherein the catheter is capable of being introduced into a body only after the protecting and constraining sheaths are removed from the scaffold.

2. The apparatus of claim 1, wherein each of the two edges extend over an entire length of the constraining sheath.

3. The apparatus of claim 2, wherein the edges are spaced by between 50 Degrees and 150 Degrees.

4. The apparatus of claim 1, wherein edges of the halves are not within the opening.

5. The apparatus of claim 1, wherein a thickness of the protecting sheath is about 50% of a thickness of the constraining sheath.

6. The apparatus of claim 1, wherein the constraining sheath is configured for being removed from the scaffold by pinching the constraining sheath, or by peeling the two edges of the constraining sheath away from each other as the constraining sheath is lifted off the scaffold.

7. The apparatus of claim 6, wherein the constraining sheath is not configured for being moved longitudinally relative to the scaffold when the constraining sheath is being removed from the scaffold.

8. The apparatus of claim 1, wherein the first half is fully covered by the constraining sheath and the second half is only partially covered by the constraining sheath.

9. The apparatus of claim 1, wherein the protecting sheath comprises a single sheath having a slit or opening extending along two sides.

10. The apparatus of claim 1, wherein each of the concave outer surfaces are formed by a pair of longitudinally extending ridges.

11. The apparatus of claim 10, wherein the opening is between one of the pair of ridges forming one of the concave outer surfaces and one of the pair of ridges forming the other of the concave outer surfaces.

12. An apparatus, comprising:
a catheter including a scaffold crimped to a balloon; a sheath disposed over the scaffold and configured for being pinched or peeled away when removed from the scaffold, the sheath comprising:
two edges defining an opening, the edges being circumferentially spaced from each other by between 5 Degrees and 150 Degrees; and
a notch on a surface of the sheath and separating the sheath into first and second portions, each portion extending from the notch to one of the edges, wherein the notch facilitates a folding, kinking or buckling of the sheath at the notch when the sheath is pinched or peeled away;
wherein the scaffold occupies a space between the notch and the opening; and
wherein the catheter is capable of being introduced into a body only after the sheath is removed from the scaffold.

13. The apparatus of claim 12, wherein an outer surface of the sheath comprises two ridges.

14. The apparatus of claim 12, wherein the notch extends over a length of the sheath.

15. The apparatus of claim 12, wherein the notch is formed on an inner or outer surface of the sheath.

16. The apparatus of claim 12, wherein the sheath is a constraining sheath, further comprising a protecting sheath disposed between the constraining sheath and the scaffold.

17. The apparatus of claim 12, wherein the sheath further comprises two pair of ridges located on opposite sides of the notch.

18. The apparatus of claim 17, wherein each pair of ridges forms a concave surface.

19. A tube comprising the apparatus of claim 1 contained within a lumen of the tube.

20. An apparatus, comprising:
a catheter including a scaffold crimped to a balloon;
a sheath disposed over the scaffold, the sheath comprising
two edges defining an opening,
two pair of two ridges extending in a longitudinal direction, wherein a concave surface extends from a first ridge to a second ridge of each of the pair of ridges, and each of the pair of ridges is located between two convex surfaces, and
a notch on a surface of the sheath and disposed between the concave surfaces.

* * * * *